(12) United States Patent
Dudziak et al.

(10) Patent No.: US 8,252,161 B2
(45) Date of Patent: Aug. 28, 2012

(54) ELECTROFILTRATION METHOD

(75) Inventors: Gregor Dudziak, Oakland, CA (US);
Michael Traving, Burscheid (DE);
Martina Mutter, Köln (DE)

(73) Assignee: Bayer Technology Services GmbH,
Leverkusen (DE)

( * ) Notice: Subject to any disclaimer, the term of this patent is extended or adjusted under 35 U.S.C. 154(b) by 1189 days.

(21) Appl. No.: 11/817,461

(22) PCT Filed: Mar. 6, 2006

(86) PCT No.: PCT/EP2006/002012
§ 371 (c)(1),
(2), (4) Date: Nov. 14, 2007

(87) PCT Pub. No.: WO2006/097212
PCT Pub. Date: Sep. 21, 2006

(65) Prior Publication Data
US 2008/0156648 A1    Jul. 3, 2008

(30) Foreign Application Priority Data
Mar. 18, 2005   (DE) .......................... 10 2005 012 594

(51) Int. Cl.
*B01D 61/42* (2006.01)
*B01D 57/02* (2006.01)
*C07K 1/26* (2006.01)
(52) U.S. Cl. ...... 204/543; 204/518; 204/544; 435/173.9
(58) Field of Classification Search .................. 204/518, 204/543, 544; 435/173.9
See application file for complete search history.

(56) References Cited

U.S. PATENT DOCUMENTS

| 3,079,318 A | 1/1959 | Bier |
| 3,989,613 A | 11/1976 | Gritzner |
| 5,087,338 A | 2/1992 | Perry et al. |
| 5,429,746 A | 7/1995 | Shadle et al. |
| 5,437,774 A | 8/1995 | Lausten |
| 2005/0072675 A1* | 4/2005 | Dudziak et al. ............... 204/518 |

FOREIGN PATENT DOCUMENTS

| AU | 601040 | 8/1990 |
| DE | 102 53 483 | 5/2004 |
| EP | 0 091 784 A1 | 10/1983 |
| EP | 0 369 945 A1 | 5/1990 |
| WO | 99 62937 | 12/1999 |

OTHER PUBLICATIONS

"Regulate" definition. Retrieved via <http://www.google.com> on Apr. 13, 2012.*
Huotari et al; "Electrically enhanced crossflow membrane filtration of oily waste water using the membrane as a cathode"; Journal of Membrane Science, Elsevier Science, 156, No. 1; Apr. 24, 1999, pp. 49-60.

* cited by examiner

*Primary Examiner* — Keith Hendricks
*Assistant Examiner* — Steven A. Friday
(74) *Attorney, Agent, or Firm* — Norris McLaughlin & Marcus PA

(57) ABSTRACT

Method for improving selectivity and productivity during purification of charged macromolecules and particles by electrofiltration by means of membranes in the electric filed. The ratio between the electric field and the permeate flow through the membrane is kept constant.

9 Claims, 3 Drawing Sheets

ELECTROFILTRATION METHOD

This is a 371 of PCT/EP2006/002012 filed Mar. 6, 2006 (international filing date).

The invention relates to a method for improving the selectivity and productivity in the purification of charged macromolecules and particles by electrofiltration by means of membranes in an electric field. The ratio of the abovementioned electric field and the permeate flow through the membrane is kept constant.

BACKGROUND OF THE INVENTION

The use of membrane electrophoresis and of electrofiltration as preparative separation techniques has been investigated since the 50 s.

In both methods, separation chambers are separated from one another by semipermeable membranes.

In membrane electrophoresis, migration of dissolved ions and dispersed, charged particles and agglomerates takes place in an electric field, but substantially no liquid flows through the separation membrane. The driving force for the transport of the material is the electric field.

In electrofiltration, a hydrostatic pressure difference is built up between the separation chambers in addition to the electric field, so that a liquid flow through the separation membrane is induced. Driving forces for the transport of material are therefore the electric field as well as the pressure difference between the separation chambers.

The electrofiltration was first mentioned by Bier, 1959, U.S. Pat. No. 3,079,318, as so-called "Forced Flow Electrophoresis". It was used for reducing the blocking of membranes in the filtration of yeast but also in the depletion of cells and albumin from blood.

U.S. Pat. No. 3,989,613 (Gritzner 1976) describes a membrane electrophoresis method in which the two streams (feed and permeate) flow in parallel. The flow velocity in the separation chambers is very low (<0.01 cm/s). This results in a relatively poor heat discharge and nonturbulent flow, which in turn leads to undesired concentration polarization. Nonselective separation membranes are used.

A further publication on electrofiltration is the dissertation thesis by Tison, 1986, Selective cascade electrofiltration. This is concerned with the separation of IgG from human blood plasma by means of electrofiltration. However, since the IgG-depleted plasma is to be returned to humans, the mode of operation at physiological saline concentration was chosen. The desalination is thus carried out neither before nor during the process, and the mode of operation has constant current and constant pressure. Owing to the high conductivity of the blood plasma, however, only low productivities can be realized.

The method of electrofiltration was further investigated by Perry et al., 1992, U.S. Pat. No. 5,087,338. Perry describes the separation efficiency of electrofiltration by means of protein-containing model solutions with respect to the selectivity. Biomolecules whose isoelectric points have a difference of 0.1 can be separated. In the examples disclosed, the method is operated at constant current. Since the conductivity of the greatly diluted feed solutions is very low and hardly differs from that of the other buffers in the permeate channel and in the electrode compartments, conductivity changes can hardly occur in the feed solution. These are laboratory-scale applications with model substances, which are not relevant in practice. In contrast, changes in the conductivity occur in practice.

In U.S. Pat. No. 5,437,774, of 1993, Laustsen explains the so-called "Electrodialysis of molecules having a high molecular weight". Starting from the separation technique of dialysis, he describes the possible design of the cell with one or more separation membranes and different chambers for diluate and concentrate. The membranes may be both uncharged membranes and ion exchange membranes. The process can be operated without permeate flow through the membrane (classical membrane electrophoresis) or with a flow forced by pressure, also described below as electrofiltration. This can be operated in the abovementioned design or with a plurality of channels in parallel, with the result that the membrane area and thus the cost-efficiency of the method are increased, as well as by possibly carrying out a plurality of separation steps in succession. In a working example, Laustsen describes the separation of BSA and hemoglobin. The procedure operates at constant voltage and constant pressure (transmembrane pressure of 67 mbar) at a comparatively high voltage (160V) and low transmembrane flow (0.1 to 0.2 m/s). On the industrial scale, this parameter combination would lead to problems with the removal of heat and to concentration polarization of the proteins at the separation membranes.

A patent application of the company Gradipore (1999, WO A 99/62937) entitled "Purification of Antibodies" describes the purification of antibodies, especially monoclonal antibodies, from peritoneal water of mice with the aid of membrane electrophoresis and the so-called Gradiflow technology (AU A 601040). The pH of the solution was adjusted so that the antibody is present in uncharged form and the charged impurities are electrophoretically depleted through the membrane.

In order to carry out the purification of the antibody, i.e. the depletion of the impurities, as completely as possible, the experiment can be interrupted and the concentrate volume exchanged or the experiment can be carried out in two stages, the pH of the solution, the pore size of the membrane and the direction of the electric field being adapted accordingly. The method is carried out at constant voltage of 200 V. On the industrial scale, the resulting high electric field strength would lead to problems with heat removal and to concentration polarization and protein denaturing at the membrane.

A similar method is disclosed in 2004 in DE A 102 534 83. In this application, a laboratory plant which can be scaled up is presented for the first time (receiver volume of 1 l). By means of a flow velocity of 5.2 cm/s in the separation chambers, sufficiently high heat discharge can be ensured. Membranes form electrically charged double layers at the solid/liquid interface by diffusion of ions out of the membrane into an aqueous medium. The use of porous membranes therefore induces in the electric field an electroosmotic pressure which produces a liquid flow through precisely this membrane. In order to compensate this electroosmotic flow, an exactly tailored electroosmotic pressure is superposed on one of the separation chambers in this method. As a result of the compensation of the electroosmotic flow, the productivity and especially the selectivity of an electrophoretic method can be significantly improved.

Furthermore, DE A 0 40 07 848, "Vorrichtung und Verfahren für die Membranelektrophorese und Elektrofiltration [Apparatus and method for membrane electrophoresis and electrofiltration]", describes a membrane module with which a protein separation can preferably be carried out by means of membrane electrophoresis or electrofiltration. An advantage here is the closed, tightly joined design, which ensure high transmembrane flow velocities in the separation channels, a minimization of dead spaces and high compactness. The laid-open application also describes the basic use of the modules for electrofiltration. The choice and optimization of the operating parameters, such as, for example, hydrostatic pressure and electric field strength, are not a subject of this laid-open application.

Usually, antibodies are carried out by a certain method explained in more detail in the U.S. Pat. No. 5,429,746, Shadle et al. "Antibody Purification" of 1995.

There are a certain number of purification steps which are used in one or other combination and sequence.

The key step of this method is product recovery and concentration from the fermentation medium. This consists as a rule of concentration and rebuffering by means of ultrafiltration, followed by an affinity chromatography step. The latter is highly selective but has a number of disadvantages on the industrial scale. Examples which will be mentioned are:

the high price of the chromatography medium the danger of washing out the toxic ligand protein A, which requires an after treatment (as a rule an additional chromatography step)

the low pH in the elution (<3), which entails a further step of rebuffering in order to be able to subject the medium to the following steps of the method.

Product recovery (capturing) is followed as a rule by at least two further chromatography steps (purification and polishing).

The methods described to date for the purification of antibodies thus have a number of disadvantages:

Classical Methods:

The conventional purification of proteins from a fermentation is effected at least using the above-described number of process steps. These complex processes are associated with high costs, which can be reduced by the novel method according to the invention.

Electrophoretic Methods Generally:

Membrane electrophoresis and electrofiltration have not been carried out to date on the industrial or production scale. In addition, model solutions having a conductivity which is substantially below that of a liquid with physiological saline concentrations, such as, for example, that of a cell culture medium, were chosen in the majority of cases.

Electrofiltration:

Experiments on electrofiltration were operated in the past with either constant current or constant voltage. Since biotechnological media and product solutions in the process have a relatively high conductivity, a reduction thereof during the electrofiltration is required in order to achieve the high mobility in the electric field and hence a high productivity of the process. Thus, in order to be able at all to realize such a process other than on the laboratory scale and other than with a model solution, the following must be noted:

In addition to the productivity, the selectivity is a further target parameter of the electrofiltration process. The selectivity of the separation in turn depends decisively on the pressure-driven transport of material through the separation membrane and on migration velocity of the proteins in the feed channel. Migration of dissolved ions in an electric field can be directed either in the same direction as or in the opposite direction to the pressure-driven transport of material. The target parameters productivity and selectivity can now be optimized for the given process by means of the operating parameters voltage and hydrostatic pressure. The operating parameters are chosen as a function of the physical properties of the dissolved components (for example, isoelectric point, molar mass, effective charge at chosen pH) and of the medium (for example, conductivity). However, if the conductivity of the medium in the feed channel changes, the optimum operating point cannot be maintained with constant operating parameters.

The problem is to be explained for the example of an electrofiltration method in which a monoclonal antibody is to be retained in the feed solution while the secondary components are depleted through the separation membrane. The pH of the solution is chosen so that the monoclonal antibody has a negative charge. Hydrostatic pressure and electric voltage are now chosen so that the migration velocity of the monoclonal antibody in the electric field corresponds at least to the permeate velocity of the medium through the membrane and is in the opposite direction to it. Secondary components which are neutral or have a positive charge are depleted through the separation membrane.

If the solution for the permeate chamber with a physiological conductivity which corresponds to that of the cell culture medium (about 10 mS/cm) is used, the optimum ratio of migration velocity of the antibody and permeation velocity of the medium through the separation medium can be maintained over the entire course of the experiment. The selectivity is therefore constantly optimum during the entire course of the experiment. Owing to the high conductivities and a limited heat discharge, however, only a relatively low productivity can be achieved.

If, however, a solution of low conductivity is used for the permeate chamber in order to desalinate the cell culture medium in the feed channel, the conductivity of the medium in the feed channel in the course of the experiment matches that of the permeate channel. During operation at constant voltage, the migration velocity of the antibody increases owing to the increasing electric field strength in the feed channel. Increasing productivity can, however, hardly be realized at constant hydrostatic pressure. If, on the other hand, the hydrostatic pressure is chosen to be higher from the beginning of the experiment, increased productivity is achieved. However, the selectivity of the method is lower at the beginning of the method and the antibody yield is reduced.

It is therefore the object of the invention to provide a method for purifying charged macromolecules, the operating parameters of which can be adapted so that the target parameters productivity and selectivity are at the chosen optimums over the entire course of the experiment.

The macromolecule-containing, in particular protein-containing, medium, in particular an antibody-containing fermentation medium, is to be concentrated by means of electrofiltration and the secondary components present in the fermentation supernatant are to be separated from the target protein.

SUMMARY OF THE INVENTION

The invention therefore relates to a method for purifying the charged macromolecules and particles by electrofiltration by means of membranes in an electric field, by means of which the selectivity and productivity are improved in the entire course.

This is effected by a particularly adapted process which is characterized by a procedure with a constant ratio of permeate flow and field strength.

For this purpose, either the process is preferably operated at constant current or a certain current profile is specified for the course of the experiment or the current is regulated as a function of the conductivity of the feed medium.

Alternatively, the process can be operated at constant field strength, based on the feed channel, or a certain field strength profile is specified for the feed channel or the field strength or the field channel is regulated as a function of the conductivity of the feed medium.

The permeate flow through the separation membrane is regulated so that a constant, optimum ratio of field strength to permeate flow is achieved.

If the product is to be purified from a solution having a physiological saline concentration, i.e. relatively high conductivity, both the field strength in the feed channel and the permeate flow are simultaneously adapted, in particular increased, preferably in the course of the reduction of the conductivity in the feed channel by desalination, so that both parameters are always in a constant ratio to one another.

DETAILED DESCRIPTION

The electric field E is generally described as $$E = \frac{U}{d}$$

U being the applied voltage and d the electrode spacing.

The following equation is used for calculating the field strength in the feed channel:

$$U_{Feed} = R_{Feed} \cdot I = \frac{1}{C_{Feed}} \cdot I$$

with the conductivity C and the current I.

It follows for the electric field in the feed channel:

$$E_{Feed} = \left(\frac{1}{C_{Feed}} \cdot I\right) \bigg/ d$$

The conductivity of the feed medium is measured in a flow cell. The current to be applied can be calculated and appropriately set. This regulation is realized with the aid of an automation unit and an externally controllable power unit.

The permeate flow is kept at a constant ratio to the field strength in the feed channel. The regulation of the permeate flow can be effected, for example, by means of pressure application to the receiver or by appropriate adjustment of the volume rates in the feed and permeate channels.

The above-described matching of electric field strength in the feed channel and the permeate flow via the membrane was realized on a laboratory plant.

By operating the electrofiltration at a constant ratio of field strength in the feed channel to permeate flow and by optimizing the operating parameters, it was surprisingly possible to improve productivity and selectivity in the purification of macromolecules.

The method according to the invention for purifying charged macromolecules and particles by electrofiltration by means of membranes in an electric field is operated so that the ratio of abovementioned electric field in the feed channel and the permeate flow through the membrane is kept constant, for example by automated monitoring.

The electric field appears from 500 to 5000 V/m, preferably from 1000 to 2000 V/m. The field strength should be adjusted so that the field generated is sufficient to move the charged molecules to be depleted out of the feed channel and into the permeate channel in an appropriate time and at the same time to keep the molecules which are oppositely charged and therefore to be retained in the feed channel. A suitable field strength must be determined in preliminary experiments for electrofiltration. In this case, suitable means not only the conditions described above but also keeping the temperature at from 0 to 40° C., in particular from 6 to 25° C., in order to avoid denaturing the charged macromolecules, in particular biomolecules.

The permeate stream is from 5 to 100, preferably from 10 to 30, $l/(h*m^2)$.

By means of this process, one or more of the following macromolecular, in particular biomacromolecular, substances can be treated: proteins, peptides, DNA, RNA, oligonucleotides, oligo- and polysaccharides, viruses, virus constituents, cells, cell constituents, enantiomers, diastereomers.

The abovementioned biomacromolecular substances may be proteins, in particular monoclonal or polyclonal antibodies.

The membrane used has a pore size of from 1 to 1000 nm, preferably from 10 to 500 nm, and preferably consists of one of the following materials: cellulose ester, polyacrylonitrile, polyamide, polyether, polyether sulfone, polypropylene, polysulfone, polyvinyl alcohol, polyvinylidene fluoride, or of alumina, silica, titanium oxide, zirconium oxide and mixed ceramics of the abovementioned oxides.

The conductivity of the starting solution, which is a mixture of different charged macromolecules or particles, but preferably of cell culture supernatant of a fermentation, is usually from 20 mS/cm to 0.5 mS/cm, particularly from 12 to 1.5 mS/cm.

In the course of the method, the conductivity is preferably reduced to 3 to 0.5 mS/cm.

The process can also be carried out as a continuously operated method. Here, continuously means firstly the realization of a connection of a plurality of electrophoresis modules in a cascade or christmas tree structure, the operating parameters described in more detail above changing during the startup process as a function of time and thereafter space, i.e. in the various membrane modules. Secondly, the continuous procedure means the operation of an electrophoresis module with continuous removal and supply of a part-stream, corresponding to diafiltration. The operating parameters likewise change as a function of time during the start up process until a steady state is reached.

The cell culture supernatant can be used directly but is preferably freed from cell residues by prefiltration by means of a microfiltration membrane.

The cell culture supernatant can be concentrated by means of ultrafiltration.

The electrolytes used in the feed, permeate and electrode wash circulation consist of a combination of weak acids and weak bases, weak acids and strong bases or strong acids and weak bases.

The electrolyte solutions preferably contain one or more of the following substances: boric acid, phosphoric acid, N-2-(acetamido)-2-aminoethanesulfonic acid, N-2-(acetamido) iminodiacetic acid, alanine, 2-amino-2-methyl-1,3-propanediol, ammonia, N,N-bis(2-hydroxyethyl)-2-aminoethanesulfonic acid, N,N-bis(2-hydroxyethyl)glycine, 2,2-bis(hydroxyethyl)iminotris (hydroxymethyl)methane, 2-(cyclohexylamino)ethanesulfonic acid, acetic acid, glycine, glycylglycine, 2-[4-(2-hydroxyethyl)1-piperazinyl] ethanesulfonic acid, 3-[4-(2-hydroxyethyl)1-piperazinyl] propanesulfonic acid, histidine, imidazole, lactic acid, 2-morpholinoethanesulfonic acid, 2-morpholinopropanesulfonic acid, piperazine-1,4-bis(2-ethanesulfonic acid), N-[tris(hydroxymethyl)methyl]-2-aminoethanesulfonic acid, N-[tris(hydroxymethyl)methyl]glycine, triethanolamine, tris(hydroxymethyl)aminomethane, citric acid.

The pH of the buffer systems is from 3 to 11.

The electrolyte solution is an aqueous solution for providing a certain ion load which permits charge transport by the electric field, and a buffer system for setting a defined pH in the solution and keeping said pH constant.

The stability of the macromolecules should be determined in preliminary experiments by preparing them in the various electrolyte solutions at different concentrations, salt contents and temperatures and observing the precipitation or agglomeration of the macromolecules, preferably of the biomolecules. The observation takes place visually and by measurement of the protein content via a chromatographic analysis method.

The electrofiltration method can be followed, if necessary, by a further membrane electrophoresis step which serves for further purification of a macromolecule under different process conditions, for example at a changed pH.

The method can also be operated as a combination of the steps comprising desalination and concentration without application of an electric field, followed by an electrofiltration. Both steps can be carried out in the same plant using the same membrane modules.

The method can also be operated as a combination of a membrane electrophoresis for partial desalination or rebuffering and subsequent electrofiltration for separation of the charged macromolecules.

All method variants described can be operated both in a batch procedure, i.e. discontinuously, and in a feed & bleed procedure, i.e. continuously.

The method in all variants described can be used for process intensification in the purification of biomolecules, in particular proteins, very particularly antibodies.

BRIEF DESCRIPTION OF THE DRAWINGS

The invention is explained in more detail or illustrated below with reference to the figures and the examples, which, however do not limit the invention.

EXAMPLES

Figure 1:
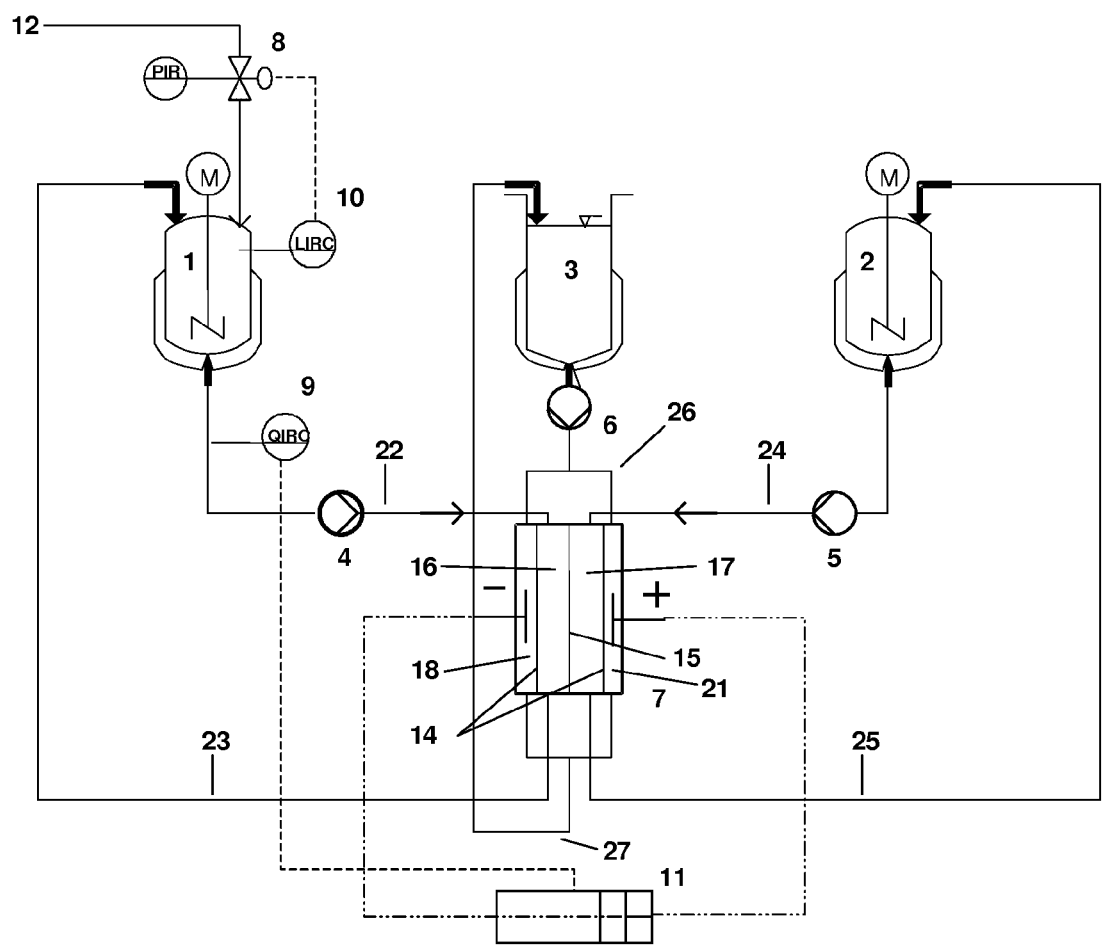
FIG. 1 shows the diagram of an electrofiltration plant with automatic regulation of the electric field and of the device for pressure control, which serves for regulating the permeate flow.

The plant used in the examples described below (FIG. 1) consists of one thermostatable receiver each for concentrate 1, permeate 2 and electrode buffer 3. The solutions are recirculated by means of pumps 4, 5, 6 via forward-flow lines 22, 24, 26 and return lines 23, 25, 27 and flow through an electrophoresis separation module 7. The pressure application in the gas space of the concentrate chamber for adjusting the permeate flow via the membrane with nitrogen from line 12 is effected by means of downstream pressure controller 8. The downstream pressure controller in turn is regulated via level probe 10.

Figure 2:
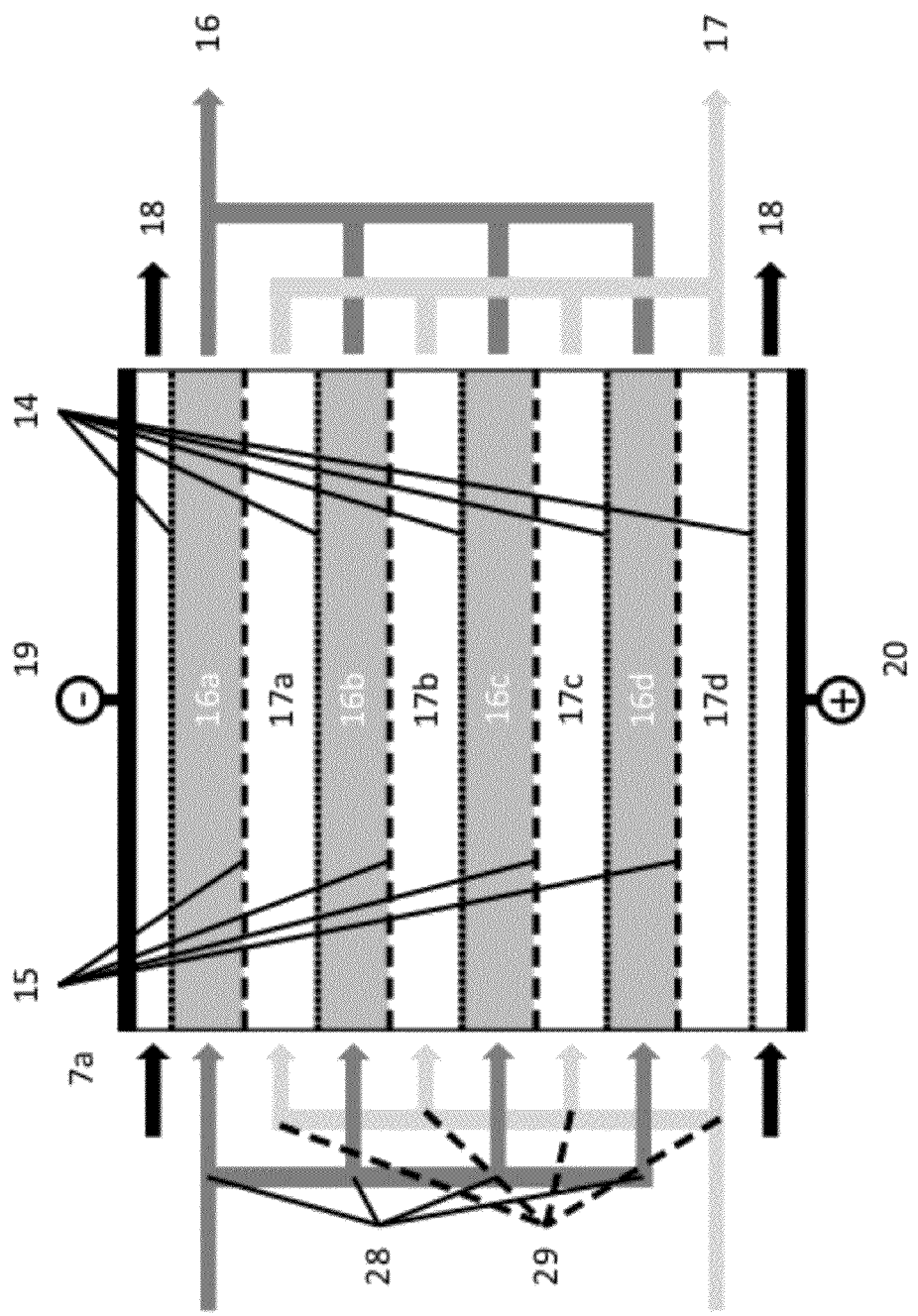
FIG. 2 shows the diagram of a membrane module in a multichannel design

The electrofiltration plant contains a module 7a having (cf. FIG. 2) in each case four parallel concentrate chambers 16a-d and permeate chambers 17a-d. The concentrate chambers 16 and permeate chambers 17 have parallel incoming flow via liquid distributors 28, 29 and are bounded by restriction membranes 14 and separation membranes 15. Here, concentrate and permeate chambers may contain nets or woven fabrics which are not shown and which act as spacers between the membranes and as baffles. The electrode chambers 18, 21 have parallel incoming flow and are bounded by restriction membranes 14. An electric field is built up by electrodes 19, 20. The electric field can be built up as shown in FIG. 2 or in the opposite direction. The electric field is regulated via the measured conductivity 9 in the concentrate feed line 22 at the external automation unit and is set on power unit 11. The permeate flow via the membrane is adapted by calculating the actually applied electric field in the upstream, likewise via the measured conductivity 9 in the concentrate feed line 22 and via the ratio of actual field strength reached at each time and desired field strength and application of this ratio to the permeate rate by the external automation unit.

Example

The plant shown in FIG. 1 and the module 7a outlined in FIG. 2 were used for separating and concentrating a monoclonal antibody. The product-containing cell culture medium was separated from the cells and cell parts after fermentation by means of ultrafiltration (pore size of the membrane 2 μm). This antibody is a IgG type which was expressed in a hybridoma cell and fermented in a stirred 0.8 l bioreactor. The antibody has an isoelectric point of 6.5 and a size of 150 kD.

The module 7a is our own development with an effective membrane area of 48 $cm^2$ per membrane layer and is described in more detail in patent application DE A 0 40 07 848, Vorrichtung und Verfahren für die Membranelektrophorese und Elektrofiltration [Apparatus and method for membrane electrophoresis and electrofiltration].

The module 7a comprises at least one first retaining plate, a first electrode chamber with electrode, at least one entrance and exit chamber each, a second electrode chamber with electrode and a second retaining plate, the chambers being separated from one another by sheet-like membrane sections cut to size, and at least the membranes being combined in their edge regions by a sealing frame to form a tightly joined module and the sealing frame having channels for the feed and removal of liquids, with passages leading away to selected chambers, and connecting channels which correspond to the respective channels in the sealing frame being present in at least one retaining plate.

A TRIS/citric acid buffer (34.4 mM TRIS and 7.5 mM citric acid, pH 8.0, conductivity 1.53 mS/cm) was used. The receiver for permeate solution 2 was filled with 1000 ml of buffer solution and that of the electrode wash solution 3 likewise with 1000 ml of buffer solution. The concentrate receiver was filled with 1500 ml of cell culture supernatant (pH 8).

The experiment was carried out at temperatures of from 6 to 10° C.

The separation module is equipped with restriction membranes 14 having a nominal cut-off of 10 kDa and separation membranes 15 having a nominal cut-off of 300 kDa.

The experiment was carried out with increasing field strength up to a maximum value of 1500 V/m, a negative potential being applied to the electrode 20 on the concentrate side. At the same time, the permeate flow was increased to a maximum value of $30 l/(h*m^2)$, field strength and permeate flow being in a constant ratio. The volume flows in the concentrate and permeate circulation were in each case 320 ml/min, corresponding to a transmembrane flow velocity of 5.2 cm/s, and the volume flow rate in the electrode circulation was 550 ml/min. The antibody concentrations were determined by means of HPLC via a protein A column. The total protein concentration as a measure of the depletion of the secondary components was analyzed by means of the BCA (bicinchinonic acid) method and by preparation of reducing SDS-PAGE gels.

The following experiment was carried out:

Electrofiltration with increasing electric field and permeate rate via the membrane increasing in relation.

Table 1 contains the test parameters and concentration curves of the example.

TABLE 1

| Run time min | Field strength US E V/m | Volume ml | Secondary components Total mass mg | mAB Total mass mg | Ratio mAB/SC | mAB Total concentration mg/l | Permeate rate P L/h * m$^2$ | Ratio P/E (L/h * m$^2$)/(V/m) |
|---|---|---|---|---|---|---|---|---|
| 0 | 413 | 1458 | 1273 | 79 | 1.0 | 54 | | |
| 15 | 449 | 1453 | | | | | | |
| 30 | 458 | 1392 | 1150 | 78 | 1.1 | 55 | 12.8 | 0.028 |
| 45 | 548 | 1349 | | | | | 9.1 | 0.017 |
| 60 | 598 | 1292 | | 73 | | 56 | 12.0 | 0.020 |
| 75 | 644 | 1252 | | | | | 8.4 | 0.013 |
| 90 | 693 | 1192 | 894 | 69 | 1.2 | 57 | 12.6 | 0.018 |
| 105 | 782 | 1127 | | | | | 13.7 | 0.018 |
| 120 | 833 | 1054 | | 65 | | 60 | 15.4 | 0.018 |
| 135 | 972 | 971 | | | | | 17.5 | 0.018 |
| 150 | 1032 | 906 | 659 | 62 | 1.5 | 66 | 13.7 | 0.013 |
| 165 | 1210 | 810 | | | | | 20.2 | 0.017 |
| 180 | 1357 | 719 | | 59 | | 79 | 19.2 | 0.014 |
| 195 | 1340 | 550 | | | | | 35.6 | 0.027 |
| 210 | 1492 | 445 | 308 | 59 | 3.1 | 98 | 22.1 | 0.015 |
| 225 | 1491 | 350 | | | | | 20.0 | 0.013 |
| 240 | 1445 | 170 | 136 | 59 | 6.9 | 144 | 37.9 | 0.026 | mAB = monoclonal antibody
SC = secondary components

Figure 3:
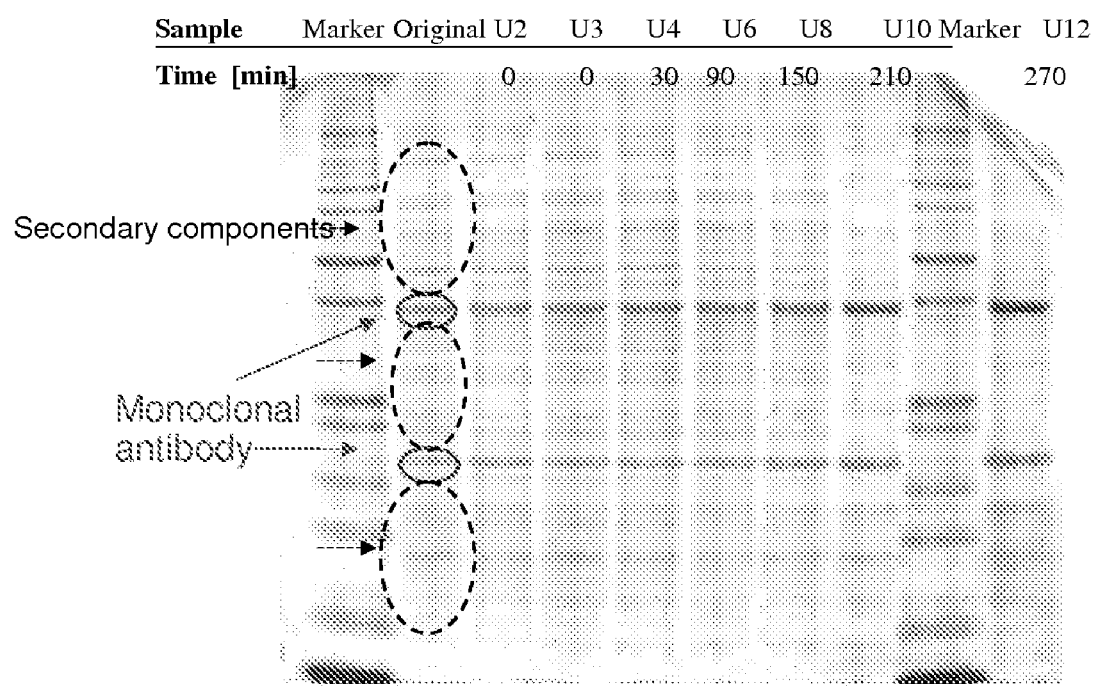
FIG. 3 shows SDS-PAGE gel under reducing conditions, for example

FIG. 3 shows SDS-PAGE gel under reducing conditions. U2 to U12 are upstream samples at different times in the experiment.

For the depletion of secondary components, the result is a mass-based depleted fraction of 0.89 after 240 minutes, at a concentration factor of the concentrate of 8.6 and an antibody yield of 0.74.

There is therefore a selectivity of 7.3 over the entire course of Example 2, with $m/m_0$ (HSA): mass-based residual fraction of HSA in the concentrate [-]

$m/m_0$ (IgG): mass-based residual fraction of IgG in the concentrate [-]

$$\psi = \frac{\ln[m/m_0(HSA)]}{\ln[m/m_0(IgG)]} : \text{selectivity} \quad [-]$$

The invention claimed is:

1. A method for improving the selectivity and productivity in the purification of a substance comprising charged macromolecules and particles in an electrolyte solution of said substance by electrofiltration from feed media wherein the conductivity of said media changes during said purification by means of a separation membrane in an electric field, wherein the ratio of the strength of the abovementioned electric field to the permeate flow rate through the separation membrane is kept constant and the field strength on the feed side of the membrane in the feed channel is changed in inverse proportion to the changes in the conductivity of the feed medium.

2. The method as claimed in claim 1, wherein the electric field strength is from 500 to 5000 V/m.

3. The method as claimed in claim 1, wherein the permeate flow rate between concentrate chamber and permeate chamber is adjusted to keep said ratio of the strength of said electrical field to the permeate flow rate through the separation membrane constant.

4. The method as claimed in claim 1, wherein the substance being purified is one or more members of the group consisting of proteins, peptides, DNA, RNA, oligonucleotides, oligo- and polysaccharides, viruses, virus constituents, cells, cell constituents, enantiomers and diastereomers.

5. The method as claimed in claim 4, wherein said substance is proteins, said proteins being monoclonal or polyclonal antibodies.

6. The method as claimed in claim 1, wherein the membranes have a pore size of from 1 to 1000 nm.

7. The method as claimed in claim 1, wherein the conductivity of said electrolyte solution is from 20 to 0.5 mS/cm.

8. The method as claimed in claim 1, wherein the electrolytes in said electrolyte solution are a combination of weak acids and weak bases, weak acids and strong bases or strong acids and weak bases.

9. The method as claimed in claim 1, wherein the electrolyte solution contains one or more substances selected from the group consisting of boric acid, phosphoric acid, N-2-(acetamido)-2-aminoethanesulfonic acid, N-2-(acetamido) iminodiacetic acid, alanine, 2-amino-2-methyl-1,3-propanediol, ammonia, N,N-bis(2-hydroxyethyl)-2-aminoethanesulfonic acid, N,N-bis(2-hydroxyethyl)glycine, 2,2-bis(hydroxyethyl)iminotris (hydroxymethyl)-methane, 2-(cyclohexylamino)ethanesulfonic acid, acetic acid, glycine, glycylglycine, 2-[4-(2-hydroxyethyl)1-piperazinyl] ethanesulfonic acid, 3-[4-(2-hydroxyethyl)1-piperazinyl] propanesulfonic acid, histidine, imidazole, lactic acid, 2-morpholinoethanesulfonic acid, 2-morpholinopropanesulfonic acid, piperazine-1,4-bis(2-ethanesulfonic acid), N[tris(hydroxymethyl)methyl]-2-aminoethanesulfonic acid, N-[tris(hydroxymethyl)methyl]glycine, triethanolamine, tris (hydroxymethyl)aminomethane and citric acid.

* * * * *